United States Patent [19]

Coleman et al.

[11] Patent Number: 4,935,406

[45] Date of Patent: Jun. 19, 1990

[54] USE OF BISMUTH (PHOSPH/SULF)ATED SACCHARIDES AGAINST CAMPLYOBACTER-ASSOCIATED GASTROINTESTINAL DISORDERS

[75] Inventors: James C. Coleman, Lenexa; Douglas L. Cole, Stanley, both of Kans.

[73] Assignee: Marion Laboratories, Inc., Kansas City, Mo.

[21] Appl. No.: 246,755

[22] Filed: Sep. 20, 1988

[51] Int. Cl.$^5$ .................. A61K 31/715; C07H 15/00; C07H 23/00; C07H 11/04
[52] U.S. Cl. ................................. 514/54; 536/17.1; 536/121; 536/117
[58] Field of Search ................ 514/54; 536/17.1, 121, 536/117

[56] References Cited

U.S. PATENT DOCUMENTS 3,432,489  3/1969  Nitta et al. ........................ 260/234

FOREIGN PATENT DOCUMENTS 0206627 12/1986 European Pat. Off. .
0230023  7/1987 European Pat. Off. .
8605981 10/1986 PCT Int'l Appl. .

OTHER PUBLICATIONS

Bowen et al., U.S. patent application Ser. No. 07/209,372, file Jun. 21, 1988.
Graham et al., *The American Journal of Gastroenterology*, 82, 283-286 (1987).
Blaser, *Gastroenterology*, 93, 371-83 (1987).
*Scrip* (Dec. 3, 1986), "Anti-Ulcer Market".
Borsch, *Leber, Magen, Darm*.(W. Ger.), 18, 38-45 (Jan., 1988).
Anderson et al. (Eds.), *Chem. Sources U.S.A.*, Directories Publishing Co., Inc., Ormond Beach, Fla. (1984), pp. 158, 257, 259, 262, 311, 326, 447 & 467.
Carey et al., *Advanced Organic Chemistry, Part B: Reactions and Synthesis*, Plenum Press, New York (1977), pp. 482-496 & 507.

*Primary Examiner*—Ronald W. Griffin
*Assistant Examiner*—Everett White
*Attorney, Agent, or Firm*—Christopher J. Rudy

[57] ABSTRACT

Bismuth (phosph/sulf)ated saccharides are useful in ameliorating gastrointestinal disorders associated with Campylobacter-like organisms such as, for example, *Campylobacter pylori*. For example, compositions containing a complex salt of bismuth hydroxide sucrose octasulfate can be thus employed to treat Type B gastritis.

8 Claims, No Drawings

USE OF BISMUTH (PHOSPH/SULF)ATED SACCHARIDES AGAINST CAMPLYOBACTER-ASSOCIATED GASTROINTESTINAL DISORDERS

FIELD

This invention especially concerns use of bismuth phosphorylated and/or sulfonated saccharides. These saccharides are generally useful against Campylobacter-associated gastric disorders.

BACKGROUND

Bowen et al., U.S. Pat. application Ser. No. 07/209,372 filed on June 21, 1988, discloses bismuth (phosph/sulf)ated saccharides. In nature and gist, these compositions are bismuth phosphorylated and/or sulfonated saccharides, which are useful as pharmaceuticals in ameliorating disorders associated with gastric mucosal damage.

Marshall, Eur. Pat. application No. 0 206 627 published on December 30, 1986, publishes methods for the treatment of gastrointestinal disorders. The methods of that publication comprise treatment of humans or lower animals, having an infectious gastrointestinal disorder, by administering bismuth, preferably as a pharmaceutically acceptable salt. The disorder may be caused or mediated by Campylobacter-like organisms, e.g., *Campylobacter pylori*.

Borody, PCT Int. Publ. No. WO 86/05981 published on October 23, 1986, publishes a treatment of non-ulcer dyspepsia with bismuth salts. The dyspepsia is associated with *Campylobacter pylori* infection, and the administration of the bismuth salts in association with antibiotics was reported to be preferred and particularly efficacious.

Graham et al., *The American Journal of Gastroenterology*, 82, 283-6 (1987), reports on *Campylobacter pylori* gastritis: The past, the present, and speculations about the future. See also, Blaser, *Gastroenterology*, 93, 371-83 (1987).

*Scrip* (December 3, 1986) reports on bacteria and the anti-ulcer market, which speculates on the possibility of a spurt in the growth of bismuth products due to the theory that *Campylobacter pylori* infection is associated with ulcer development, and which also specifically reports on use of De-Nol ® plus an antibiotic. But see, Borsch, *Leber. Magen. Darm.* (W. Ger.), 18, 38–45 (January, 1988), which reports on therapy for *Campylobacter pylori* infection. Borsch reports that a simple and efficient therapy eradicating *Campylobacter pylori* with high reliability from gastroduodenal mucosae is unknown, and that bismuth salts might play an important future role in a more pragmatic approach which investigates any potential clinical benefit derived from a suppression of bacterial growth possibly resulting in a temporary restoration of the mucosal integrity, but that this approach will probably fail to modify the long-term natural history of *Campylobacter pylori*-associated chronic gastritis and its sequelae.

SUMMARY

The present invention provides a method for ameliorating a gastrointestinal disorder of a subject associated with a Campylobacter-like organism population comprising administering an effective amount of a bismuth (phosph/sulf)ated saccharide to the subject under conditions such that said disorder is ameliorated.

Notably, the present inventive method not only can most significantly reduce populations of the Campylobacter-like organism, but also, it can provide a most significantly effective decrease in inflammation of treated gastrointestinal mucosa. Further significant advantages inherently attend this invention as well.

ILLUSTRATIVE DETAIL

In general, the bismuth (phosph/sulf)ated saccharides employed in the practice of this invention are selected from the compositions of the mentioned Bowen et al. invention, which thus contain such a component as bismuth, and of which a full description follows herein. The bismuth (phosph/sulf)ated saccharides further contain such a component as a phosphorylated and/or a sulfonated saccharide, which is a saccharide generally having more than one moiety selected from such moieties as at least one of phosphate and sulfate moieties esterified thereto.

The component such as bismuth includes such metallic elements as bismuth and pharmaceutically acceptable compounds therewith. The pharmaceutically acceptable compounds with bismuth include, of course, molecular level covalent or ionic complexes with bismuth and the phosphated and/or sulfated saccharide moieties, molecular level covalent or ionic complexes with such bismuth-containing moieties or compounds as bismuth hydroxides and the phosphated and/or sulfated saccharide moieties, these compositions in the presence of a suitable pharmceutical carrier, and so forth and the like.

The component such as a sulfate ester and/or a phosphate ester saccharide includes thus such saccharides as 1) sulfated saccharides, 2) phosphated saccharides, 3) sulfated-phosphated saccharides, and 4) mixtures thereof. Saccharide conponents having at least three sulfate ester moieties per saccharide nucleus are desirably employed. Polysulfated saccharides are more typically employed in the practice of this invention. The polysulfated saccharides desirably contain substantial amounts of persulfated saccharides.

Saccharide moieties themselves which may be employed in the practice of this invention include mono-, di-, tri-, tetra- and oligosaccharides. Examples of suitable saccharide nuclei or moieties may be selected from appropriate residues of such saccharides as erythrose, threose, arabinose, deoxyribose, fructose, glucose, ribose, mannose, lactose, cellobiose, maltose, sucrose, trehalose, melezitose, stachyose, and so forth and the like. The saccharide moieties desirably are disaccharides of pentoses and/or hexoses. Sucrose is preferred.

The bismuth (phosph/sulf)ated saccharides may be a composite mixture, i.e., a composition combining more than one chemical entity to make up the composition. They may be considered complex bismuth salts of (phosph/sulf)ated saccharide(s).

The bismuth (phosph/sulf)ated saccharides are generally insoluble in water, lower alcohols, e.g., methanol, lower ketones, e.g., acetone, dilute aqueous hydrocloric acid, e.g., 0.1 N, with generally no gelling propensity in acidic water. They may be semi-crystalline in the solid state.

Significantly, the bismuth (phosph/sulf)ated saccharides employed in the practice of this invention are generally and quite surprisingly soluble in appropriate aqueous ammonia solutions. This is most notably significant because the vicinity surrounding such Campylobacter-like organisms as, for example, *Campylobacter pylori* is typically ammoniacal, particularly in vivo. See e.g., Graham et al., supra., at page 284, and Blaser, supra., at page 378.

In general, the bismuth (phosph/sulf)ated saccharide can be prepared by contacting a hydrogen (phosph/sulf)ated saccharide and a bismuth substance. Conditions are those sufficient to form the bismuth (phosph/sulf)ated saccharide employed in the practice of this invention.

In general, the hydrogen (phosph/sulf)ated saccharide is a saccharide analogous to that of the corresponding bismuth (phosph/sulf)ated saccharide but having phosphoric and sulfonic acid moieties bonded therewith. Sulfonic acids are preferred.

The hydrogen (phosph/sulf)ated saccharides can be obtained or can be prepared by known procedures or by procedures analogous thereto. For example, the following hydrogen (phosph/sulf)ated saccharides are in general commercially available:
2'-deoxy-α-D-ribose-1-phosphate;
2'-deoxyribose-5'-phosphate;
D-fructose-1-phosphate;
D-fructose-6-phosphate;
D-fructose-1,6-diphosphate;
α-D-galactose-1-phosphate;
D-galactose-6-phosphate;
galactose-6-sulfate;
glucose-1-phosphate;
D-glucose-1-phosphate;
glucose-6-phosphate;
D-glucose-6-phosphate;
glucose-1,6-diphosphate;
D-glucose-6-sulfate (sodium salt);
α-mannose-6-phosphate;
α-lactose-phosphate (barium salt). See e.g., Anderson et al. (Eds.), *Chem Sources U.S.A.*, Directories Publishing Co., Inc., Ormond Beach, Fla. (1984). Also, phosphorylation and/or sulfonation may be accomplished on corresponding saccharides having appropriate esterfication site(s) available, as is known in the art. For example, phosphorylation may be accomplished by appropriate treatment of the reactant saccharide with a suitable phosphorylating agent, e.g., one which may be phosphoryl chloride or cyanoethyl phosphate. See e.g., Carey et al., *Advanced Organic Chemistry, Part B: Reactions and Synthesis*, Plenum Press, New York (1977) at pages 482–96 & 507. Sulfonation may be accomplished by appropriate treatment of the reactant saccharide with a suitable sulfating agent, e.g., chlorosulfonic acid, anhydrous sulfuric acid or sulfur trixode-pyridine complex in a solvent such as pyridine, formamide, dimethyl formamide, chloroform or liquid sulfur dioxide. See e.g., Nitta et al., US 3432489. See also, Michaeli, EP 0230023, especially for preparations with sodium and potassium sulfate saccharides.

Metal salts of the (phosph/sulf)ated saccharides may be converted to the hydrogen (phosph/sulf)ated saccharides by known procedures. For example, ion exchange procedures with an ion exchange resin such as a sulfonated divinyl benzene resin in its hydrogen ion form may be thus employed, passing the metal salts, desirably the potassium salts, over the resin in a suitable media, e.g., water, especially in a highly pure water in an about 20:1 weight-weight ratio of the water to metal salt, at room temperature in order to prepare the hydrogen (phosph/sulf)ated saccharides. The thus-prepared hydrogen (phosph/sulf)ated saccharides may be cooled to about 10° C. or so or kept at temperatures about from 20 to 30° C. at this stage, if desired.

In general, the bismuth substance contains bismuth, which, when contacted with the hydrogen (phosph/sulf)ated saccharide, can form the bismuth (phosph/sulf)ated saccharide. As an illustration, the bismuth substance may be bismuth hydroxide $(Bi(OH)_3)$. Freshly prepared $Bi(OH)_3$ is preferred. Commercially available $Bi(OH)_3$ may contain $Bi_2O_3$ and may not work as well in the practice of this invention.

Typically, the hydrogen (phosph/sulf)ated saccharide is dispersed or dissolved in a suitable medium, e.g., water, for the contact. Concentrations of the hydrogen (phosph/sulf)ated saccharide may vary widely, but higher aqueous concentrations, at accordingly low pH values, e.g., pH 1.5, may advantageously be employed. Temperatures can be about from 10 to 30° C., but may advantageously be about room temperature, e.g., about 25° C. The bismuth substance is contacted with the hydrogen saccharide dispersion or solution. Typically, the bismuth substance is a solid, and it may advantageously be stirred into the dispersion or solution of the hydrogen (phosph/sulf)ated saccharide, typically in water. Alternatively, for example, the bismuth substance may be slurried in water as a sample of fine particles, with the typically aqueous dispersion or solution of the hydrogen (phosph/sulf)ated saccharide being added thereto, e.g., slowly as from immediate prepartion from the mentioned ion exchange procedure using an ion exchange column. Amounts of the hydrogen (phosph/sulf)ated saccharide may advantageously be in a stoichiometric eqivalent excess in comparison to the bismuth substance, e.g., about from above 100 to 160 percent of theory or more in such an excess. Thus accordingly, e.g., the bismuth substance may be used in a molar ratio of about from 5:1 to 8:1 in comparison to the hydrogen (phosph/sulf)ated saccharide. Cooling during this contact step may be undertaken if desired, but it is not generally necessary if the contact is carried out at about room temperature. This mixture may be allowed to be stirred for a time, say, about from a score (20) minutes to an hour or so, e.g., about half an hour. The bismuth (phosph/sulf)ated saccharide product is typically recovered as a solid.

The recovery of the product may advantageously be carried out by suction filtration and washing, with vacuum drying. The washing may generally be with such liquids as, e.g., water, methanol and/or acetone, etc. The product may be slurried in methanol and/or acetone and suction filtered therefrom if desired. Heating of the product to dry it should be avoided because temperatures above usual ambient temperatures, e.g., 45° C., may cause decomposition of the desired product. The product is thus advantageously stored under refrigeration, e.g., in a freezer, generally with cautionary protection from exposure to actinic radiation as may be provided with an amber or opaque glass bottle.

The method for use of the bismuth (phosph/sulf)ated saccharide in the practice of this invention generally involves treating a gastrointestinal disorder of a subject associated with a Campylobacter-like organism by administering an amount of the bismuth (phosph/sulf)ated saccharide effective to ameliorate the disorder. Preferably, the effect is substantial, or is even great.

The administration is preferably oral.

The subject can be a human patient.

The gastrointestinal disorder typically includes or is so-called Type B gastritis. See e.g., Graham et al., supra., at page 283.

Suitable amounts of the bismuth (phosph/sulf)ated saccharide include those which may be in doses about from 5 to 100 mg per kg body weight of the subject per dose, say, about 20 mg/kg/dose. Also in human patients, an estimated range of 0.5 to 10 grams per day is contemplated. Divided doses per day are typical, often, say, four oral doses per day, especially with human patients.

Dosage forms of the bismuth (phosph/sulf)ated saccharide may include such unit dosage forms as tablets, capsules and appropiate suspensions. Tablet forms may be advantageously employed because of ease of manufacture and administration.

In general, the Campylobacter-like organism can be any such organism or the like which is the object which appropriately responds to the method of this invention. Campylobacter-like organisms may include those known as such in the art. See e.g., Marshall, EP 0206627 at page 4 & Blaser, supra. A Campylobacter-like organism population may contain a notable population of *Camoylobacter pylori*. Typically, *Campylobacter pylori* and its associated gastrointestinal disorders, e.g., the Type B gastritis, are advantageously treated effectively.

The following examples further illustrate the invention. Percentages are by weight unless otherwise specified.

Example A illustrates preparation of bismuth (phosph/sulf)ated saccharide. Examples 1 & 2 illustrate use of this product as it pertains to the practice of this invention.

EXAMPLE A

To a 12-L 3-necked flask fitted with a mechanical stirrer and separatory/addition funnel was charged 1750 mL of glacial acetic acid and 3500 mL of Nanopure TM water as obtained by passing deionized water through a NANOpure II (Barnstead) column. To the acid mixture was added 500 g of $Bi(NO_2)_3.5H_2O$. The mixture was stirred to dissolve the solid. Next, with cooling, 3500 mL of concentrated (28%) $NH_4OH$ (aq.) was slowly added. The pH of the mixture became alkaline. Solid product was collected by filtration. The filtered solid was washed with Nanopure TM water and next with methanol. The filtered solid was dried under vacuum at 50° C., which yielded 253.2 g of product $Bi(OH)_3$ (94.6 percent of theory).

A sample of 1600 g of Amberlite IR-120 ion exchange resin which had been washed with 2-3 bed volumes of 1N HCl (aq.) was loaded onto a column. The loaded resin was washed with Nanopure TM water until the pH became nearly that of the water and until no chloride precipitate was observed with argentous nitrate.

A sample of 80 g of potassium sucrocose octasulfate ($K_8SOS$), which was previously prepared according to Examples 1 & 2 of Michaeli, EP 0230023, was dissolved in about 1400 mL of Nanopure TM water. This $K_8SOS$ solution was loaded onto the resin of the column and was eluted fairly rapidly with 4 L of "nanopure" water.

Effluent from the column was directed to a 12-L 3-necked flask containing a slurry of the above $Bi(OH)_3$ in 1 L of Nanopure TM water. The slurry was cooled by an ice-water bath. The latter reaction mixture was next stirred for 30 minutes; whereupon it was filtered slowly with suction with several Buchner funnels. Suction was maintained overnight, and upon drying the product was ground to a finely divided state. The yield of product was 139.42 g (95.5 percent of theory). The product was odorless, white, semi-crystalline as determined by x-ray powder diffraction procedures, was insoluble in water, 0–1 N HCl(aq.), methanol and acetone, was soluble in 4N sulfuric acid (aq.) and soluble in trifluoroacetic acid but decomposed gradually in these latter two acid media, and had the following composition:

Octasulfate content: 88.6 percent (HPLC & EA);
Heptasulfate content: 5.4 percent (HPLC & EA);
Hydroxide content as, e.g., $Bi(OH)_3$: 5.9 percent (HPLC & EA);
Bismuth content: 58.6 percent (AA & EA);
Water content: ca. 7.8 percent (Difference & Karl Fisher);
Microorganisms: None detected (Microbial bioburden).

The molecular structure was confirmed by Fourier transform infrared spectroscopy (FT-IR), by high pressure liquid chromatography (HPLC) against a known reference standard of potassium sucrose octasulfate ($K_8SOS.7H_2O$) and by atomic absorbtion spectroscopy (AA). Elemental analyses (EA) were employed in the above. Thus, the product may be considered to be a bismuth hydroxide salt of sucrose octasulfate substantially of empirical composition: $[Bi(OH)_2]_8SOS$.

EXAMPLE 1

The effectiveness of the $[Bi(OH)_2]_8SOS$ as from Example A as a Campylobacter-like organism growth inhibiting agent was determined by examining its actions in agar gel, proceeding by the Kirby-Bauer technique. Two isolates of *Campylobacter pylori* were obtained from human biopsy stomach tissue, and both were separately cultivated on agar gel samples which had the requisite well formed therein. Wells were filled with either a dilute aqueous ammonium hydroxide solution, which was a 10:1 mixture by volume of water and standard concentrated aqueous ammonium hydroxide (28 to 30 percent $NH_3$, or ca. 58 percent $NH_4OH$) or [Bi(OH)] SOS dissolved in the dilute aqueous solution. The agar samples were checked for inhibition of growth of the *Campylobacter pylori* surrounding the wells. An inhibition zone value of 10 mm or more is considered to be significant inhibition. The following results were observed.

| STUDY | Agar well zone inhibition zones in $[Bi(OH)_2]_8SOS$ Dil. $NH_4(OH)$ | Dilute $NH_4OH$ |
|---|---|---|
| 1 | 16 mm | 0 mm |
| 2 | 18 mm, 18 mm, 16 mm | 0 mm |

This demonstrates that the bismuth (phosph/sulf)ated saccharides are not only effective in inhibiting the growth of Campylobacter-like organisms, but also, they are also generally capable of being dissolved in dilute aqueous ammonia solutions. This is surprising and unexpected, and it is highly significant because, as mentioned before, the immediate area surrounding a colony of these organisms in in vivo gastrointestinal mucosa is believed to have dilute aqueous ammonia present due to its production by the organisms. Moreover, the bismuth (phosph/sulf)ated saccharides are unexpectedly capable of being pharmaceutically effective in such dilute aqueous ammoniacal environments against the campylobacter-like organisms.

EXAMPLE 2

An objective of this study was to determine if the [Bi(OH)$_2$]$_8$SOS of Example A would amelioriate manifestations of *Campylobacter pylori*-associated gastritis in gnotobiotic piglets. The study was conducted in a generally blind format, and thus, the [Bi(OH)$_2$]$_8$SOS is referred to in this example as "drug."

A litter of gnotobiotic piglets was derived by routine methods, birthed on Day 1, and was divided into 3 groups as follows: Group I (Piglet Nos. 1–5); Group II (Piglet Nos. 6–10); and Group III (Piglet No. 11). Each piglet weighed at least approximately 1 kg at birth. All piglets of Groups I and II were orally infected with about 10$^9$ Colony Forming Unit of *Campylobacter pylori* broth culture on Day 7 after pre-treatment with cimetidine, which brought the stomach pH upward to reflect a more conducive environment for the introduction of the *Campylobacter pylori*. The piglet in Group III, the uninfected and untreated control, was housed in a separate isolation unit.

Ten days after infection (Day 17), treatment was initiated for all piglets of Group I. For this, 2.0 gm of drug was suspended in 7–10 mL of milk formula and placed in the feed pan. Thirty to forty minutes after consumption, the piglets were fed 150–200 mL of replacement milk formula. The infected, untreated piglets of Group II and the piglet of Group III received 7–10 mL of the otherwise same milk formula but without the drug. The treatment and the feedings were continued three times per day (7:30 a.m., 12:00 noon, 4:00 p.m.) for 10 days (days 18 through 27).

On Day 28, the stomach of each piglet was exteriorized, ligated at the esophagus and duodenum, transected and removed. Each stomach was opened longitudinally along the greater and lesser curvature. Gross lesions, e.g. the presence of lumenal mucus or lymphoid follicles were noted. Samples of gastric mucosa from four anatomical regions of the stomach (cardia, fundus, pylorus and antrum) were taken and streaked onto specialized agar plates for bacterial re-isolation. Adjacent full thickness samples of gastric tissue were then collected from each anatomic region, placed into individual labeled vials and fixed in 10 percent phosphate buffered formalin. Tissue samples were, respectively, trimmed, embedded in paraffin, sectioned at 5–6μ, p, and stained with hematoxylin and eosin and Warthin-Starry (W/S) stains for histologic evluation and demonstration of any organisms.

Table 1 summarizes gross anatomic findings. Changes from the normal, e.g. excess mucus and/or submucosal lymphoid follicles were detected in all 5 infected, untreated piglets (Group II) whereas, no lesions were detected in any of the five infected, treated piglets (Group I) or in the uninfected, untreated control (Group III).

TABLE 1

A summary of gross observations in gastric tissue from the gnotobiotic piglets infected with *Campylobacter pylori* and treated with the drug.

| Identification | Excess Gastric Lumenal Mucus | Lymphoid Follicles |
|---|---|---|
| Group I: (infected, treated) | | |
| Piglet No. 1 | 0 | 0 |
| Piglet No. 2 | 0 | 0 |
| Piglet No. 3 | 0 | 0 |
| Piglet No. 4 | 0 | 0 |
| Piglet No. 5 | 0 | 0 |
| Group II: (infected, untreated) | | |
| Piglet No. 6 | 1 | 3 |
| Piglet No. 7 | 1 | 0 |
| Piglet No. 8 | 0 | 2 |
| Piglet No. 9 | 0 | 2 |
| Piglet No. 10 | 0 | 1 |
| Group III: (uninfected, untreated) | | |
| Piglet No. 11 | 0 | 0 |

Table 1 is scored visually as: 0 = no lesions; 1+ = minimal change from normal; 2+ = moderate change from normal; and 3+ = severe change from normal.

Table 2 summarizes histopathologic findings. The control piglet of Group III exhibited several small inactive lymphoid follicles below the muscularis mucosae, a condition found occasionally in such uninfected piglets. Inflammatory lesions associated with *Campylobacter pylori*-induced gastritis were composed of focal and diffuse lymphoplasmacytic cellular infiltrates in the lamina propria of the gastric mucosa. Cellular aggregates ranged from small focal collections of leukocytes to large, prominent well-organized lymphoid follicles. All infected piglets from both Groups I and II exhibited histologic evidence of gastritis. However, the severity and extent of the inflammation was substantially less in the drug-treated piglets of Group I when compared to those piglets not treated with the drug (Group II).

TABLE 2

A summary of histopathologic findings in gastric tissue from the gnotobiotic piglets infected with *Campylobacter pylori* and treated with the drug.

| | Anatomical Region of the Stomach | | | |
|---|---|---|---|---|
| Identification | Cardia | Fundus | Antrum | Pylorus |
| Group I: (infected, treated) | | | | |
| Piglet No. 1 | 2 | 0 | 2 | 0 |
| Piglet No. 2 | 2 | 0 | 1 | 0 |
| Piglet No. 3 | 1 | 1 | 1 | 0 |
| Piglet No. 4 | 3 | 1 | 0 | 0 |
| Piglet No. 5 | 0 | 0 | 2 | 0 |
| Group II: (infected, untreated) | | | | |
| Piglet No. 6 | 2 | 2 | 3 | 0 |
| Piglet No. 7 | 3 | 1 | 3 | 0 |
| Piglet No. 8 | 3 | 1 | 3 | 0 |
| Piglet No. 9 | 2 | 3 | 3 | 0 |
| Piglet No. 10 | 1 | 1 | 1 | 0 |
| Group III: (uninfected, untreated) | | | | |
| Piglet No. 11 | 0 | 0 | 0 | 0 |

Table 2 is scored visually as: 0 = no microscopic lesions; 1 = minimal change from normal; 2 = moderate change from normal; and 3 = severe change from normal.

Table 3 summarizes findings related to the presence of the drug. In addition to inflammation, crystalline amorphous extracellular material indicating the presence of drug in the gastric mucus layer of all 5 treated piglets. This demonstrates that the drug was retained in the stomach tissue even on the day following cessation of treatment.

TABLE 3

A summary of the presence of the drug in the gastric lumenal mucus in the STET piglets infected with Campylobacter pylori and treated with the drug.

| Identification | Anatomical Region of the Stomach | | | |
|---|---|---|---|---|
| | Cardia | Fundus | Antrum | Pylorus |
| Group I: (infected, treated) | | | | |
| Piglet No. 1 | + | + | + | + |
| Piglet No. 2 | − | − | + | + |
| Piglet No. 3 | − | − | − | + |
| Piglet No. 4 | + | + | + | + |
| Piglet No. 5 | + | + | + | + |
| Group II: (infected, untreated) | | | | |
| Piglet No. 6 | − | − | − | − |
| Piglet No. 7 | − | − | − | − |
| Piglet No. 8 | − | − | − | − |
| Piglet No. 9 | − | − | − | − |
| Piglet No. 10 | − | − | − | − |
| Group III: (uninfected, untreated) | | | | |
| Piglet No. 11 | − | − | − | − |

Presence of amorphous, crystalline extracellular debris in gastric lumenal mucus detected histologically as "+" (present) or "−" (absent).

Table 4 summarizes microbiologic findings. Organisms were recovered from all 4 anatomic sites in all 5 infected, untreated piglets and identified as Campylobacter pylori on the basis of growth on TVAP, gram stain and urease and catalyase activity. Object organisms were not recovered from any treated piglet of Group I, nor were object organisms recovered from the control piglet of Group III. The Warthin-Starry stain delineates organisms in situ. The stain is capricious and interpretation is frequently complicated by silver grain precipitate. See, Blaser, supra., at page 378. Structures suggestive of the object organisms were observed in 4 of 5 treated piglets (Group I) and 5 of 5 untreated piglets (Group II). However, the object bacterial organisms were much more frequent in sections of mucosa from the Group II piglets.

TABLE 4

A summary of microbiologic findings in the gastric mucose of gnotobiotic piglets infected with Campylobacter pylori and treated with the drug.

| Identification | Cardia | Fundus | Antrum | Pylorus |
|---|---|---|---|---|
| Culture and Re-isolation[1] | | | | |
| Group I: (infected, treated) | | | | |
| Piglet No. 1 | 0 | 0 | 0 | 0 |
| Piglet No. 2 | 0 | 0 | 0 | 0 |
| Piglet No. 3 | 0 | 0 | 0 | 0 |
| Piglet No. 4 | 0 | 0· | 0 | 0 |
| Piglet No. 5 | 0 | 0 | 0 | 0 |
| Group II: (infected, untreated) | | | | |
| Piglet No. 6 | 3 | 3 | 3 | 2 |
| Piglet No. 7 | 2 | 2 | 3 | 2 |
| Piglet No. 8 | 1 | 1 | 2 | 1 |
| Piglet No. 9 | 1 | 2 | 3 | 2 |
| Piglet No. 10 | 2 | 3 | 3 | 2 |
| Group III: (uninfected, untreated) | | | | |
| Piglet No. 11 | − | − | − | − |
| Warthin-Starry (W/S) Stain[2] | | | | |
| Group I: (infected, treated) | | | | |
| Piglet No. 1 | + | − | − | − |
| Piglet No. 2 | − | ± | − | − |
| Piglet No. 3 | + | ± | ± | − |
| Piglet No. 4 | − | − | − | − |
| Piglet No. 5 | − | + | ± | − |
| Group II: (infected, untreated) | | | | |
| Piglet No. 6 | + | + | + | + |
| Piglet No. 7 | + | − | − | + |
| Piglet No. 8 | + | + | ± | + |
| Piglet No. 9 | ± | + | ± | + |
| Piglet No. 10 | + | + | + | + |
| Group III: (uninfected, untreated) | | | | |
| Piglet No. 11 | − | − | − | − |

[1]Data expressed as a qualitative estimate of the number of colonies on TVAP agar as 0 = no growth; 1 = minimal growth; 2 = moderate growth; and 3 = extensive growth.
[2]Data on W/S scored as + = present; − = not present, and ± = questionable.

The following conclusions were drawn:
1. The drug was generally nontoxic and well-tolerated by the piglets.
2. All piglets of Groups I and II became infected with Campylobacter pylori.
3. Treatment with the drug in general effectively eliminated culturable Campylobacter pylori from gastric mucosa ·in all anatomic locations; residual organisms were detected rarely in W/S-stained sections. It was not known if these organisms were viable, or if they were organisms vs. stain precipitate.
4. Surprisingly, treatment appeared to result in diminution of histologic lesions associated with Campylobacter pylori gastric colonization.
5. The drug appears to be very effective in the treatment of Campylobacter pylori associated gastritis in this animal model system.

Thus, the [Bi(OH)$_2$]$_8$SOS proved to be most significantly effective in the amelioration or control of Campylobacter pylori in the in vivo models used in this study. Accordingly thus, the bismuth (phosph/sulf)ated saccharides may be used generally as disclosed herein for treatment in human subjects as well.

CONCLUSION

The present invention is thus provided. Various modifications can be effected by those skilled in the art within the spirit of this invention, the asserted scope of which is particularly pointed out by the following distinctly claimed subject matter.

What is claimed is:

1. A method both for ameliorating a gastrointestinal disorder of a subject associated with Campylobacter organism population and for substantially reducing the Campylobacter organism population comprising administering an effective amount of a bismuth (phosph/sulf)ated saccharide to the subject under conditions such that both said disorder is ameliorated and said population is substantially reduced.

2. The method of claim 1, wherein the bismuth (phosph/sulf)ated saccharide contains a bismuth hydroxide (phosph/sulf)ated saccharide.

3. The method of claim 1, wherein signs of inflammation associated with the presence of the Campylobacter organism population are substantially reduced.

4. The method of claim 3, wherein the bismuth (phosph/sulf)ated saccharide contains a complex salt of bismuth hydroxide sucrose octasulfate.

5. The method of claim 3, wherein the bismuth hydroxide (phosph/sulf)ated saccharide is administered in an oral dosage form in daily amounts ranging from about 0.5 g to 10 g.

6. The method of claim 1, 2, 3 or 5 wherein the Campylobacter organism population contains a substantial population of Campylobacter pylori.

7. The method of claim 6, wherein the bismuth (phosph/sulf)ated saccharide contains a bismuth hydroxide salt of sucrose octasulfate.

8. The method of claim 1, wherein the bismuth (phosph/sulf)ated saccharide is a bismuth phosphated saccharide.

* * * * *